US00PP14393P29

(12) United States Plant Patent
Lemon et al.

(10) Patent No.: US PP14,393 P2
(45) Date of Patent: Dec. 23, 2003

(54) GERANIUM PLANT NAMED 'GLOBAL RED PEPPERMINT'

(50) Latin Name: *Pelargonium×peltatum*
Varietal Denomination: Global Red Peppermint

(75) Inventors: David Lemon, Lompoc, CA (US); Wendy Oglevee-O'Donovan, Scottdale, PA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/274,794

(22) Filed: Oct. 21, 2002

(51) Int. Cl.[7] ..... A01H 5/00

(52) U.S. Cl. ..... Plt./332

(58) Field of Search ..... Plt./332

(56) References Cited

U.S. PATENT DOCUMENTS

PP13,022 P2 * 10/2002 Utecht ..... Plt./332

* cited by examiner

*Primary Examiner*—Kent Bell
(74) *Attorney, Agent, or Firm*—Webb Ziesenheim Logsdon Orkin & Hanson PC

(57) ABSTRACT

A new and distinct ivy geranium plant with ruby red and white bicolored flowers above medium green foliage.

1 Drawing Sheet

Botanical classification: *Pelargonium×peltatum* (ivy geranium).
Varietal denomination: 'Global Red Peppermint'.

BACKGROUND OF THE INVENTION

The present invention comprises a new and distinct cultivar of *Pelargonium×peltatum* known by the varietal name 'Global Red Peppermint', Breeder No. GRUxPC. The new variety was discovered in Lompoc, Calif. The new variety is a result of cross breeding of 'Global Ruby Red' (female) (U.S. Plant Pat. No. 11,600) and 'Peppermint Candy' (male) (unpatented). The new variety exhibits similar flower color to 'Peppermint Candy'. The new variety has a growth habit similar to 'Global Ruby Red' which is more compact than that of 'Peppermint Candy'. The new variety differs from 'Global Ruby Red' primarily in flower color. The new variety was first asexually reproduced by cuttings in Connellsville, Pa. The new variety has been field trialed and has been found to retain its distinctive characteristics and remain true to type through successive propagations.

The new variety when grown in a glass greenhouse in Connellsville, Pa. using full light, 55° F. night temperature and 72° F. day temperature and grown in a soilless media with constant fertilizer at 200–250 ppm nitrogen and potassium has a response time of ten weeks from a rooted cutting to flower in a 6 inch pot.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar taken on a plant 10 weeks old from a rooted cutting. The data which defines these characteristics were collected by asexual reproductions carried out at Oglevee, Ltd. in Connellsville, Pa. The color readings were taken on May 22, 2002 indoors under 65–85 foot candles of cool white fluorescent light. Color references are primarily to The R.H.S. Colour Chart of The Royal Horticultural Society of London.

PLANT

Form: Compact, uniform cascading mound.
Height: 11–16 cm to top of foliage.
Diameter: 45 cm.
Strength: Does not require artificial support; presents a uniform cascading basket.
Rooting time: 10–14 days to visible roots.
Foliage: Stalked leaf arrangement.
Leaves:
- *Arrangement.*—Alternate.
- *Size.*—4.0–5.25 cm long; 6.0–7.0 cm wide.
- *Shape.*—Reniform; cordate base.
- *Margin.*—Entire, pedately lobed.
- *Texture.*—Leathery.
- *Pubescence.*—Slight.
- *Color.*—Upper surface: 137B. Lower surface: 137C. Zone: Present 5–7 mm from point of petiole attachment; zone is 8–12 mm wide. Color ranges in intensity from 187A to 147A.
- *Ribs and veins.*—Type: Palmate. Color: 146C.
- *Stipules.*—Two per node.

Petioles:
- *Color.*—146B.
- *Length.*—4.0–6.0 cm.

Stem/branches:
- *Color.*—146B.
- *Internode length.*—2.0–4.5 cm.

THE BUD

Characteristics just before anthesis:
- *Shape.*—Overall: Elongated elliptical cluster when no color showing. Individual bud: Elliptical or oval when no color showing.

*Size.*—Umbel: 3.0–4.0 cm across cluster of 6–9 buds. Individual bud: 1.1–1.6 cm wide; 0.4–0.6 cm long.

*Color.*—Individual bud (when closed, beginning to separate in middle): 146B, 145A at longitudinal areas; petal colors are 187A and 187 B, with some colors of 155D, 59A, and 53A.

INFLORESCENCE

Diameter of umbel: 8–10 cm.

Depth of umbel: 5.0–5.7 cm.

Borne: Umbel; flowers on pedicel; pedicel on peduncle; 5.0–8.0 cm above foliage.

Number of flowers per umbel: 6–9.

Flowers:

*Form.*—Slightly cupped.

*Size.*—4.8–5.4 cm wide; 0.8–1.1 cm deep.

*Petals.*—Shape: Inverted teardrop, heart shaped to slightly rounded apex, pointed to slightly blunt base. Size: 1.7–2.2 cm wide; 2.7–3.1 cm long. Margin: Entire. Number per flower: 10–15. Texture: Velvety; smooth; highly reflective. Color: Upper surface: Color and streaking pattern is unique to each petal; some petals are solid red, while others are nearly solid white with only a thin edge of color lining each petal. Most petals have an edging of ruby red that fades to different degrees of red and is streaked with white toward the center and base of the petal. Because of the variations in the streaking, the petals present a variety of red tones; color ranges from deep burgundy, dark red, to lighter ruby red. At the outer edge, colors range between 187A, 60A, 59A, 53A and 53B. Moving toward the center of the petal, the color fades to include 53B, 53C, 53D, 46A, 50A, 57A and 57C, 58B and 155D. Near the center of the petal there is speckling where the white streaks meet with the color. This speckling ranges in color from darker reds to light pinks and includes 61A, 61B, 58A and 58B. Near the base of the petal, the colors include 58A, 58C, 58D, 59C, 60A, 61A, 61C, 63B, 51A, 52A, 52B, and 54B. Darker veining of 58A and 61A is present on some petals. The very base of the petal is 155D. Lower surface: Outer edge of bottom petal is darkest having colors including 64A, 61A, 53B and 53C. Moving toward the center are small specks of color that compose a streaking pattern of 155D, 55B, 54A, 54C, 53D, 52A, 51A, 63B, 63C, 61C, 61D, 60C, 59C, 58A and 58C. The base of the petal is 155D. Some veining shows through.

Petaloids:

*Number.*—0–5.

*Shape.*—Irregular; some are twisted; tubular; petal shaped with cut margin; anther-like, holding pollen.

*Color.*—Same as petals.

Sepals:

*Number.*—5.

*Shape.*—Lanceolate, wider at base, slightly wide at center in some, sharp point at tip, entire and smooth margin.

*Size.*—1.4–1.5 cm in length, 0.3–0.7 cm in width.

*Color.*—146D with reflective properties of 146A.

Pedicel:

*Length.*—1.8–2.6 cm.

*Color.*—144A with anthocyanin staining of 183B on some older pedicels.

Peduncle:

*Length.*—9–15 cm.

*Color.*—144A.

Fragrance: None detected.

Disease/pest resistance: No susceptibility to diseases or pests has been noted to date.

Lasting quality: Overall bloom lasts 7–14 days.

REPRODUCTIVE ORGANS

Stamens:

*Quantity.*—3–4.

*Anthers.*—2 mm long.

*Filaments.*—Length: 9–10 mm. Color: 155D with speckling of 58A, 59A, and 60A nearer the tips.

*Pollen color.*—168A.

Pistils:

*Number.*—One.

*Length.*—1.1–1.2 cm.

*Stigma.*—Number: One. Color: 187A.

*Style.*—Length: 3–4 mm. Color: 155D.

Ovaries: Superior, 139D; 0.6 cm long, 0.2 cm wide, heavy pubescence.

Fruit: None.

I claim:

1. A new and distinct variety of ivy geranium plant substantially as shown and described.

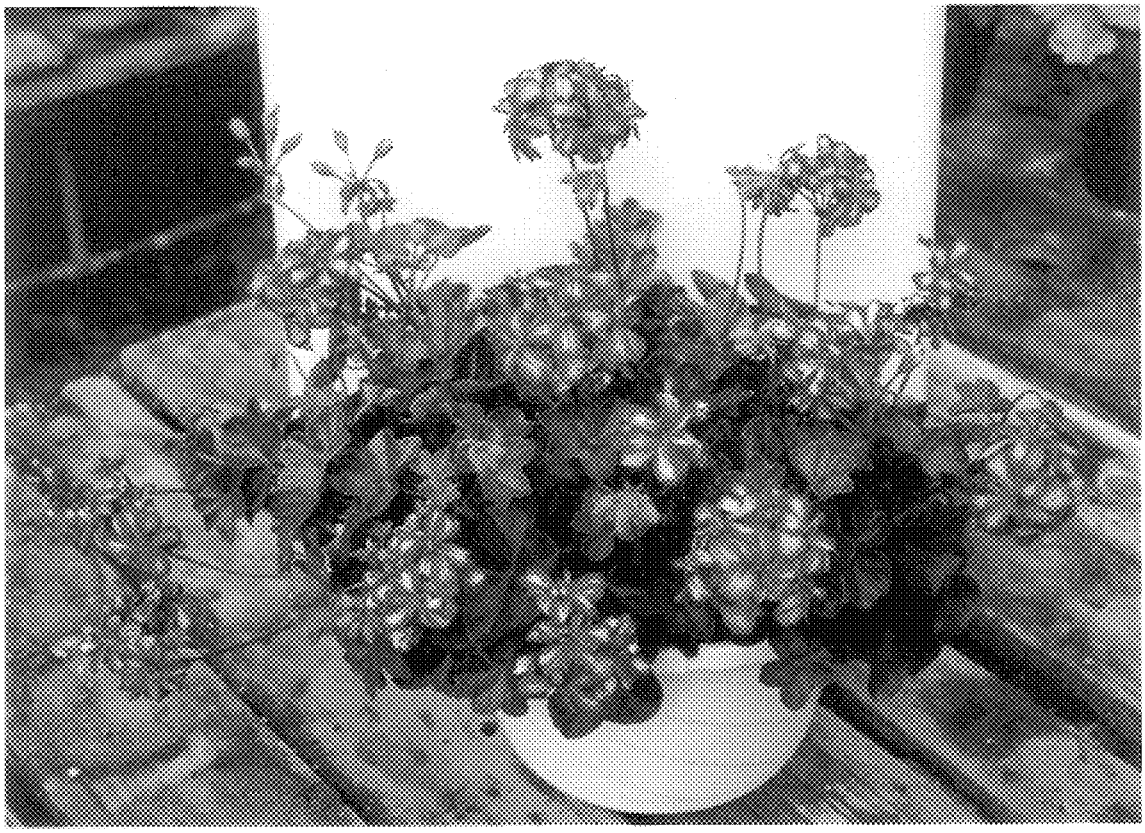

* * * * *